United States Patent
Cvetko

(10) Patent No.: US 9,741,166 B2
(45) Date of Patent: Aug. 22, 2017

(54) GENERATION AND VIEWING OF PANORAMIC IMAGES

(71) Applicant: Novarad Corporation, American Fork, UT (US)

(72) Inventor: Steven Todd Cvetko, Draper, UT (US)

(73) Assignee: Novarad Corporation, American Fork, UT (US)

( * ) Notice: Subject to any disclaimer, the term of this patent is extended or adjusted under 35 U.S.C. 154(b) by 494 days.

(21) Appl. No.: 14/088,236

(22) Filed: Nov. 22, 2013

(65) Prior Publication Data

US 2014/0146044 A1    May 29, 2014

Related U.S. Application Data

(60) Provisional application No. 61/729,580, filed on Nov. 24, 2012.

(51) Int. Cl.
| | |
|---|---|
| G06T 19/00 | (2011.01) |
| G06T 7/00 | (2017.01) |
| G06F 19/00 | (2011.01) |
| G06T 17/20 | (2006.01) |

(52) U.S. Cl.
CPC .......... G06T 19/003 (2013.01); G06F 19/321 (2013.01); G06T 7/0012 (2013.01); G06T 17/20 (2013.01); G06T 2210/41 (2013.01)

(58) Field of Classification Search
None
See application file for complete search history.

(56) References Cited

U.S. PATENT DOCUMENTS

| | | | | |
|---|---|---|---|---|
| 6,252,599 B1* | 6/2001 | Natsuko | ............... | G06T 19/006 345/419 |
| 2003/0007673 A1* | 1/2003 | Truyen | .................... | G06T 19/00 382/128 |
| 2005/0226483 A1* | 10/2005 | Geiger | ................... | G06T 15/08 382/128 |
| 2009/0244060 A1* | 10/2009 | Suhling | ................. | A61B 6/032 345/419 |
| 2014/0044329 A1* | 2/2014 | Veerman | .............. | G06T 7/0024 382/128 |

OTHER PUBLICATIONS

Lee et al., "Panoramic endoluminal display with minimal image distortion using circumferential radial ray-casting for primary three-dimensional interpretation of CT colonography", European Radiology (Impact Factor: 4.01), Mar. 2009 19(8):1951-9. DOI: 10.1007/s00330-009-1362-1.*
Ricky, "Conversion between Spherical and Cartesian Coordinates Systems" https://rbrundritt.wordpress.com/2008/10/14/conversion-between-spherical-and-cartesian-coordinates-systems/ , Oct. 14, 2008.*

* cited by examiner

*Primary Examiner* — Saptarshi Mazumder
(74) *Attorney, Agent, or Firm* — Thorpe North & Western LLP

(57) ABSTRACT

A method of creating a panoramic peripheral image may include identifying a virtual observer at a position in a modeled scene. Peripheral images of the modeled scene may be obtained, including views at multiple angles from the virtual observer. The peripheral images may be arranged to depict a panoramic peripheral view of the modeled scene.

10 Claims, 11 Drawing Sheets

GENERATION AND VIEWING OF PANORAMIC IMAGES

PRIORITY CLAIM

Priority is claimed to U.S. Provisional Patent Application Ser. No. 61/729,580, filed Nov. 24, 2012, which is hereby incorporated herein by reference in its entirety.

BACKGROUND

Early detection of cancer and other maladies is a goal of many researchers and others in the practice of medicine. Modern imaging technologies, such as CT (computed tomography) scans, x-rays, ultrasound and so forth have been used to identify maladies, with the goal of early identification for better treatment results. Early identification of a suspected tumor in a localized stage may improve chances for successful treatment and elimination of the tumor.

A large number of colorectal cancer cases are diagnosed each year, accounting for a significant number of cancer-related deaths. Successful treatment may depend, at least in part, on a stage of the cancer when the cancer is discovered. Some example treatment options include surgery, radiation, chemotherapy and so forth. Because early detection may result in simpler treatment, and where treatment of later detected cancer may increase cost, discomfort, risk of death and so forth, periodic examinations are desirable. A high percentage of colon cancers are treatable with early detection, yet tens of thousands of Americans die each year due to colon cancer where no early detection measures were taken.

A colonoscopy is an example examination which may allow the detection of cancer within the colon. Specifically, a colonoscopy may refer to a medical procedure for examining a colon to detect abnormalities such as polyps, tumors, inflammatory processes in the anatomy of the colon and so forth. One existing type of colonoscopy typically involves direct endoscopic examination of the colon with a colonoscope. The colonoscope is inserted through the patient's anus and directed along the length of the colon, thereby permitting direct endoscopic visualization of colon polyps and tumors and in some cases, providing a capability for endoscopic biopsy and polyp removal. Although colonoscopy may be a useful method for examining a colon, colonoscopy may also be time-consuming, expensive to perform, and demand a high level of skill by the medical professional performing the procedure. Because colonoscopy is an invasive procedure, there is a risk of injury to the colon as well as a risk of colon perforation and peritonitis, which can be fatal. Due to risks and discomfort involved in some examinations, such as colonoscopies, some individuals avoid potentially life-saving examinations.

DETAILED DESCRIPTION

Figure 1:
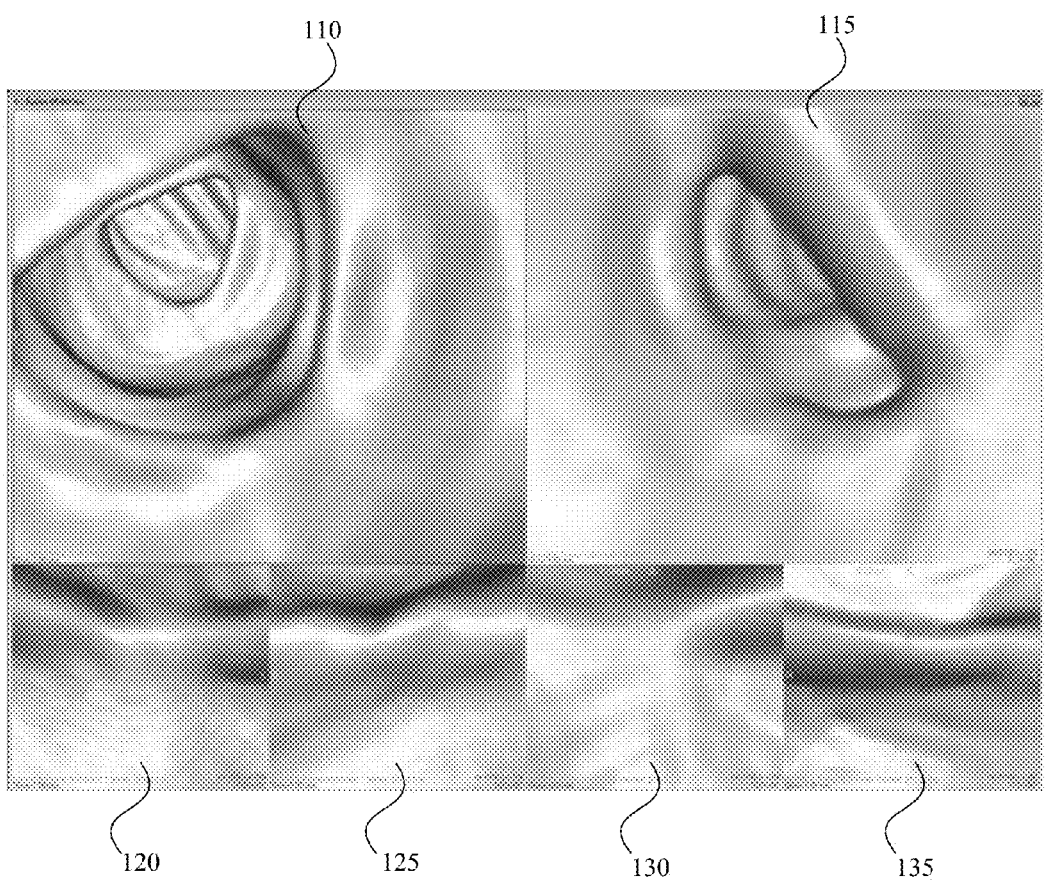
FIG. 1 is an illustration of a display window displaying anterior and posterior images of a virtual model, along with a plurality of peripheral images of the virtual model in accordance with an example of the present technology.

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

Definitions

As referred to herein, a "medical professional" may include physicians, physician assistants, nurse medical professionals, medical specialists, and any of a variety of other types of health care professionals.

As referred to herein, a "medical procedure" may include the science or practice of the diagnosis, treatment, and prevention of disease. A medical procedure may encompass a variety of health care practices intended to maintain and/or restore health by the prevention and treatment of illness in human beings. A medical procedure may also apply to tasks relating to health science, biomedical research, and medical technology to diagnose and treat injury and disease, such as through medication or surgery, as well as through therapies such as psychotherapy, traction, prostheses, biologics, ionizing radiation and so forth.

While the present technology is described in terms of medicine, the technology may alternately be applied in other areas of technology, science, etc. in which productivity is measured, such as according to a type of unit indicative of time, effort, skill, and so forth involved in completing a task.

It is noted that, as used in this specification and the appended claims, the singular forms "a," "an," and "the" include plural referents unless the context clearly dictates otherwise.

As used herein, a plurality of components may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Examples of the Technology

It is noted in the present disclosure that when describing the system, or the related devices or methods, individual or separate descriptions are considered applicable to one another, whether or not explicitly discussed in the context of a particular example or embodiment. For example, in discussing a device per se, other device, system, and/or method embodiments are also included in such discussions, and vice versa.

Furthermore, various modifications and combinations can be derived from the present disclosure and illustrations, and as such, the following figures should not be considered limiting.

A variety of imaging strategies have therefore been designed, using a variety of techniques and modalities, to aid in making an accurate diagnosis of a malady early and non-invasively, where possible.

For example, virtual colonoscopy may be performed in place of a physical colonoscopy using a colonoscope. A virtual colonoscopy may use images generated by computed tomography (CT) imaging systems where cross-sections of regions of the human body are imaged using measured attenuation of X-rays through the cross-section of the body. More specifically for purposes of a virtual colonoscopy, the CT imaging system may generate two-dimensional images of the inside of an intestine. A series of such two-dimensional images may be combined to provide a three-dimensional image of the colon.

Virtual colonoscopies may avoid some of the risks and discomforts associated with conventional colonoscopy, but may still involve patient preparation through purgatives and enemas. Virtual colonoscopies can also detect many abnormalities and potentially fatal problems outside the colon that an optical scope cannot see, such as a renal cancer, an aortic aneurism, a liver tumor, enlarged lymph nodes, metastatic disease, enlarged spleen and so forth. One issue facing some virtual colonoscopy technologies is that the accuracy of examinations and diagnosis may be less than that of a conventional, physical colonoscopy. This may be due, at least in part, to a large number of images the medical professional may examine to determine if a polyp, tumor or an abnormality exists in the colon, and/or to a presentation of the images to the medical professional in a manner which may be improved upon.

In one example, the present technology may include creation of a panoramic peripheral image. The panoramic peripheral image may be a linear panoramic peripheral image, or one which extends continuously linearly or in a straight line. For example, the linear panoramic peripheral image may be a two-dimensional image strip. A virtual observer may be identified at a position in a modeled scene. For example, the modeled scene may be a virtual colon. The virtual observer may represent a point of view, a virtual camera, etc. Peripheral images of the modeled scene may be obtained, including views at different angles from the virtual observer. The peripheral images may be arranged to depict the linear panoramic peripheral view of the modeled scene.

Referring to FIG. 1, a plurality of images of an interior of a colon are illustrated in an arrangement in accordance with an example of the present technology. The plurality of images include anterior 110 and posterior 115 views directed along a centerline or axial direction within a void in the colon. Anterior and posterior terminology is used to represent directions along the centerline of the colon towards ends of the colon (not necessarily in a straight line towards the end of the colon, but following an interior of the colon). Anterior and posterior terminology may refer to directions along which waste products travel, or may refer to directions along which a medical professional is traversing the colon along a virtual path in a virtual colonoscopy. For example, traversing the colon toward a first direction may be traversal in the anterior direction and away from the posterior direction. However, if the medical professional reverses direction, the new, reversed direction may be the anterior direction and the opposite direction becomes the posterior direction.

When viewing a three dimensional (3D) volume virtual model of a colon, a viewer may be permitted to explore the virtual model. For example, exploration of the virtual model may be analogized to a flight simulator where a pilot may fly the plane through the environment. In one example, a medical professional may be given full control of a virtual camera to manipulate the camera in different positions and orientations to achieve a desired view. The medical professional may in effect pilot a view point or the camera. The medical professional may be allowed to explore a section of interest in the virtual model while ignoring other sections. In some examples, however, to simplify exploration of the model, the medical professional may be limited to traversing a predetermined path. Use of a predetermined path may permit the medical professional to focus on the virtual space being viewed rather than concentrating on avoiding steering into walls of the virtual model.

Some virtual colonoscopies may show one or both of the anterior and posterior views while traversing the virtual colon. Because the inner walls of the colon do not provide a uniform, smooth surface, a medical professional may traverse the colon multiple times, such as in the anterior or forward direction and again in the posterior or reverse direction. Features of interest in the colon, such as polyps, cavities and so forth may be obscured from view due to ridges, structures, deformations, etc. of the colon when traversing the colon in a single direction using the posterior or anterior views. Use of both posterior and anterior views for traversal in either direction may assist in reducing the time and effort expended to fully examine the virtual colon model.

Being restricted to following a predetermined path may still lead to difficulties in fully examining a virtual model. For example, the view presented to the medical professional may be limited to what is visible in the anterior 110 and posterior 115 views without the ability to turn the camera to view side walls to more closely or thoroughly inspect areas of interest. The present technology may therefore include multiple peripheral images 120, 125, 130, 135 depicting sidewalls of the model. In other words, the images may be of views orthogonal to a direction of travel along the predetermined path (such as the centerline within a void defined by the model walls). The multiple images 120, 125, 130, 135 may be of different views from a virtual observer within the model. For example, the multiple images 120, 125, 130, 135 may include views of a top, right, left, and bottom side wall from a perspective of facing the anterior direction illustrated in the anterior view 110. The multiple images 120, 125, 130, 135 may be include any suitable number of images, including 2 or more images. In this example, four images are used. A greater number of images, such as 6 or more images, may also be used. The multiple images 120, 125, 130, 135 may be arranged linearly, or in a straight line, and may represent a panoramic peripheral view, being peripheral to the anterior or posterior directions. The peripheral images 120, 125, 130, 135 may be arranged in any particular order, or may be organized to depict the views in a specific desired order, such as left, top, right and then bottom, in order from left to right. The peripheral images 120, 125, 130, 135, as well as the anterior and posterior images 110, 115, may include labels identifying useful information, such as the direction of the view, the position within the model and so forth.

Inclusion of peripheral images 120, 125, 130, 135 in a display presented to the medical professional may enable the medical professional to simultaneously view anterior/posterior views in conjunction with views in other directions. Allowing the medical professional to view each of the available views simultaneously may facilitate more efficient and rapid examination of the model.

Figure 2:
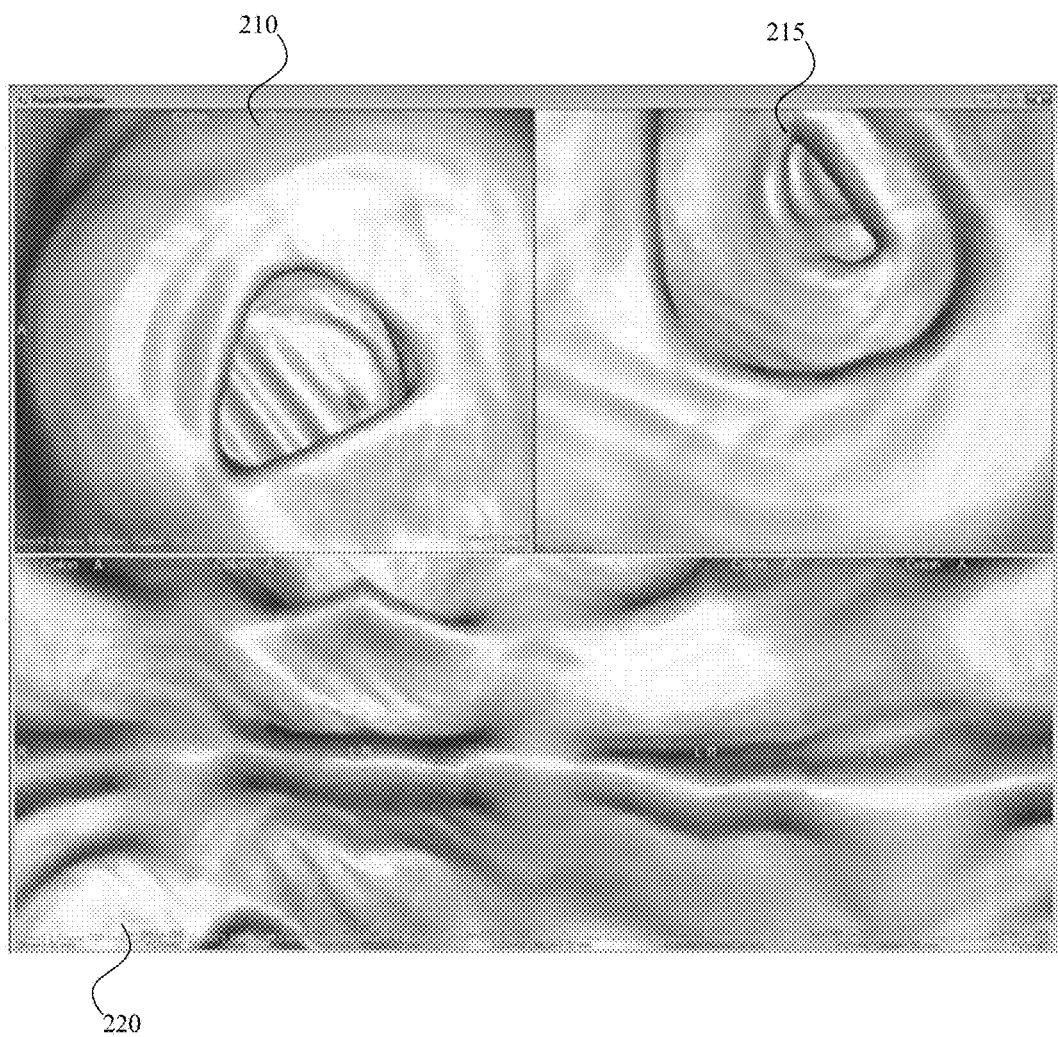
FIG. 2 is an illustration of a display window displaying anterior and posterior images of a virtual model, along with a seamless panoramic peripheral image of the virtual model in accordance with an example of the present technology.

Referring to FIG. 2, another example of the present technology is provided where a medical professional may be enabled to view a linear panoramic peripheral view 220 of the model. In this example, rather than providing multiple distinct views as in FIG. 1, where seams between the views are plainly visible, multiple peripheral images may be stitched together to form a single seamless, linear panoramic peripheral view 220 of the model. In this example, six peripheral images, rather than the four images used in FIG. 1, have been stitched together. Use of an increased number of peripheral images may more fully capture a 360° peripheral view and increase the similarity of edges of adjacent images to reduce or eliminate the appearance of seams, which seams may obscure or complicate examination of features of interest. In this example, portions of the panoramic image may be identified where the peripheral images were stitched together. The cylindrical nature of a colon virtual model may result in curvature of features that do not perfectly align when images from different views are stitched together. Scallops, jagged edges or other deformations not present in the actual colon or colon model may be present as a result. The seamless imaging aspect may be useful as compared with the seamed view in FIG. 1, but may have disadvantages if a medical professional does not recognize an aberration or deformation due to the graphical stitching. Some image processing may be applied to the linear panoramic image to smooth edges, match coloration, minimize sharpness of angles at intersections and so forth. Care may be taken not to over-process the image and potentially obscure views of polyps or other features of interest within the model.

In some ways, the panoramic view 220 in FIG. 2 may be more useful to a medical professional than the panoramic view in FIG. 1, due to the increased number of images for increased coverage and the stitching of the images to eliminate seams. In thie illustrated example, the panoramic view 220 size has been increased in proportion to the anterior posterior images 210, 215 of FIG. 2 as compared with the panoramic and anterior/posterior view proportions of FIG. 1. The panoramic view 220 of FIG. 2 may represent up to or more than a full 360° panoramic peripheral view from the virtual observer. As the virtual observer is moved along the direction of travel within the virtual colon, the panoramic view 220 may change to represent the change in position of the virtual observer. For example, as the virtual observer moves in the anterior or forward direction, the images in each of the anterior 210, posterior 215 and peripheral panoramic 220 views may be updated according to the degree of movement of the view point or virtual observer in the anterior direction.

Figure 3:
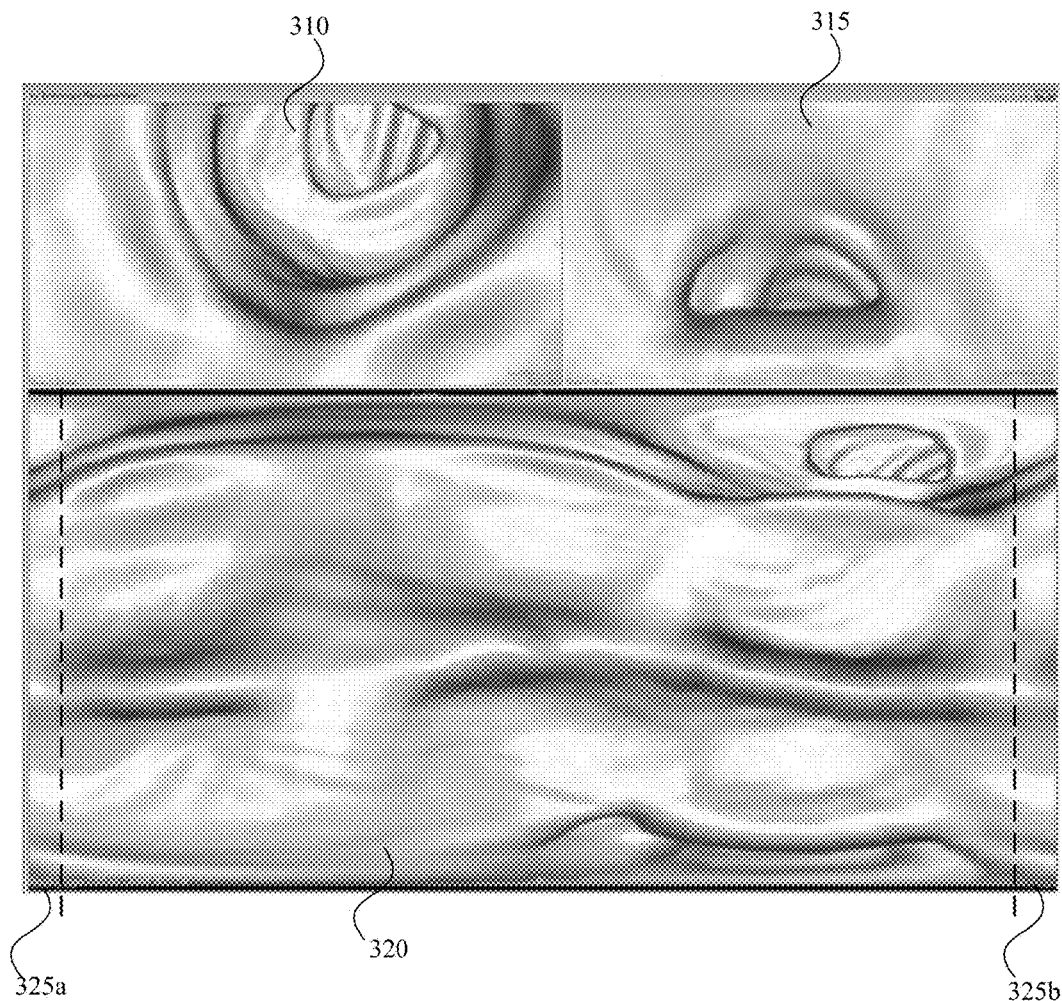
FIG. 3 is an illustration of a display window displaying anterior and posterior images of a virtual model, along with a panoramic peripheral image of the virtual model generated using spherical shells in accordance with an example of the present technology.

In accordance with another example of the present technology, the panoramic peripheral view may be rendered to avoid issues with seams, deformation and so forth. FIG. 3 represents an example display including anterior 310 and posterior 315 views, as well as a linear panoramic peripheral view 320, without seams, stitching deformations and so forth. In this example, the panoramic view 320 is greater in size, or resides on a greater portion of display real estate, than the anterior and posterior views combined. Viewing of the peripheral panorama without seams, deformations and the like may simplify the examination of the model by a medical professional significantly because the medical professional may have an assurance that features within the virtual model are accurately displayed. Furthermore, because features of interest in the virtual model are on the side walls and the side walls may represent an accurate depiction of the model, prominence of the anterior and posterior views may be reduced. The linear peripheral panoramic view 320 may provide a better tool for medical professionals in effectively examining the colon than the anterior 310 or posterior 315 views, which anterior 310 and posterior 315 views may suffer from various limitations as set forth previously.

The panoramic peripheral view 320 in FIG. 3 may optionally include a view in the anterior and posterior directions, such as at sides (i.e., top or bottom sides) of the panoramic image. The panoramic peripheral view may also include a greater than 360° view to ensure that features of interest may be viewable without falling on a seam at an edge of the image. In other words, portions 325a, 325b at sides of the panoramic view 320 may represent an overlap or duplicate of a same portion of the model.

Figure 4:
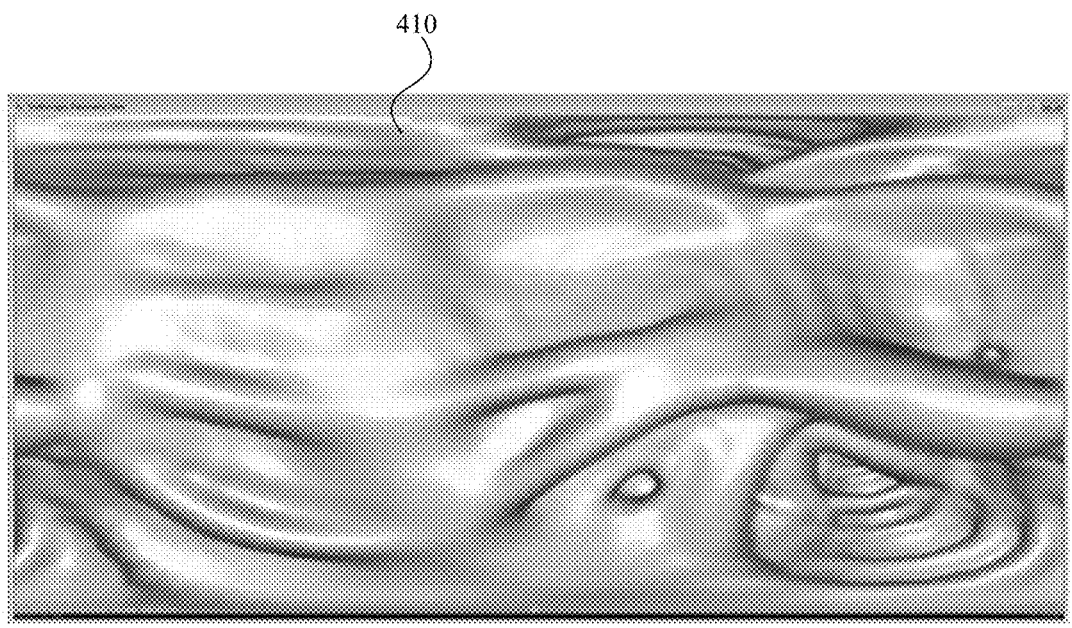
FIG. 4 is an illustration of a display window displaying a panoramic peripheral image of the virtual model generated using spherical shells in accordance with an example of the present technology.

In practice, a medical professional may find the linear panoramic peripheral view to be more valuable than anterior or posterior views, and may opt to display the panoramic peripheral view 410 without the anterior and posterior views, as illustrated in FIG. 4. Navigation of the model may still be performed along the predetermined path in the anterior or posterior directions, but rather than viewing dedicated views of the anterior or posterior directions the medical professional may view a side view or peripheral view orthogonal to a direction of travel in the model. Inclusion of dedicated anterior or posterior views may draw attention away from the peripheral views where important features may be visible. Existing virtual colonoscopies have, at least in some implementations, been displayed such that a focus of the user is drawn to the direction of travel and away from the side walls of the colon where important features may be located. Elimination of dedicated anterior or posterior views can reduce such distraction.

An explanation of how the seamless panoramic peripheral image is created will now be described. Initially, images of a desired area of the body may be obtained. For example, images of a colon may be obtained from a CT scanner. The CT scanner or other image acquisition device may be a portion of a virtual colonoscopy system or may be a separate independent component for producing the images usable by the virtual colonoscopy system. The CT images may include two-dimensional slices of the portion of the body, which may be "stacked" to form three-dimensional (3D) image data. The 3D CT images may be analyzed to identify pixels or image portions with the density of air (less than approximately −860 HU (Hounsfield Unit)). Identification of density of image portions from CT scans is commonly performed. Regularly spaced pixels of air may be collected and used as "seeds" for the next step in the process. A region-growing process may be performed starting at a seed. This process may be performed by using a queue to track neighboring pixels in the region of the seed pixels and expanding identification of air until an entire air pocket is filled, or rather until a non-air region is identified. Other seeds for air identification not consumed in the growing of a previous region may be grown into a separate region.

Figure 5:
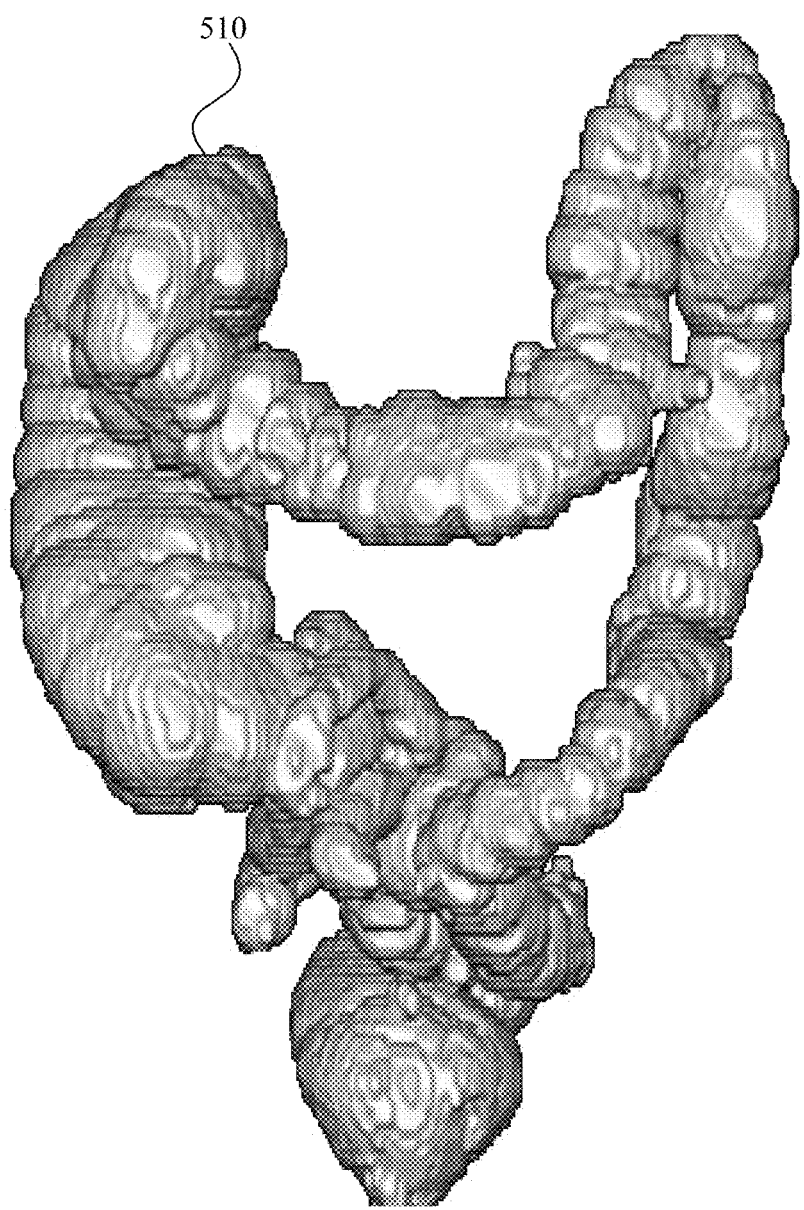
FIG. 5 is an illustration of a three-dimensional model of a virtual colon.

Many 3D regions of air found through the region-growing process may be removed after identification because the regions are not likely part of the colon. For example, identified regions may open to an area outside the body or may have a size inconsistent with the size of a colon (e.g., the regions may be too small, too large, have too small of a diameter for a colon and so forth). Regions consistent with a colon may be kept and identified for creating a 3D model of the colon. FIG. 5 represents an example 3D virtual colon model 510 identified and created using the above-described process.

To facilitate a fly-through virtual endoscopy of the colon, the "center line" or view point path through the colon may be identified from one end to another. The distance to the nearest edge of the model may be computed for every pixel inside the virtual colon. For example, this computation may be performed by reverse region-growing. In other words, the edge pixels may be placed in a queue, and then neighboring pixels of the edge pixels may be evaluated such that the region grows inward. The interior of the colon may be treated as a weighted graph where each pixel is connected or linked to neighboring pixels and the weight of the link equals the distance from the edge of the model. As an example, Dijstra's Shortest Path Algorithm may be used to identify an optimal path of pixels at every position within the model to the end of the modeled colon.

Figure 6:
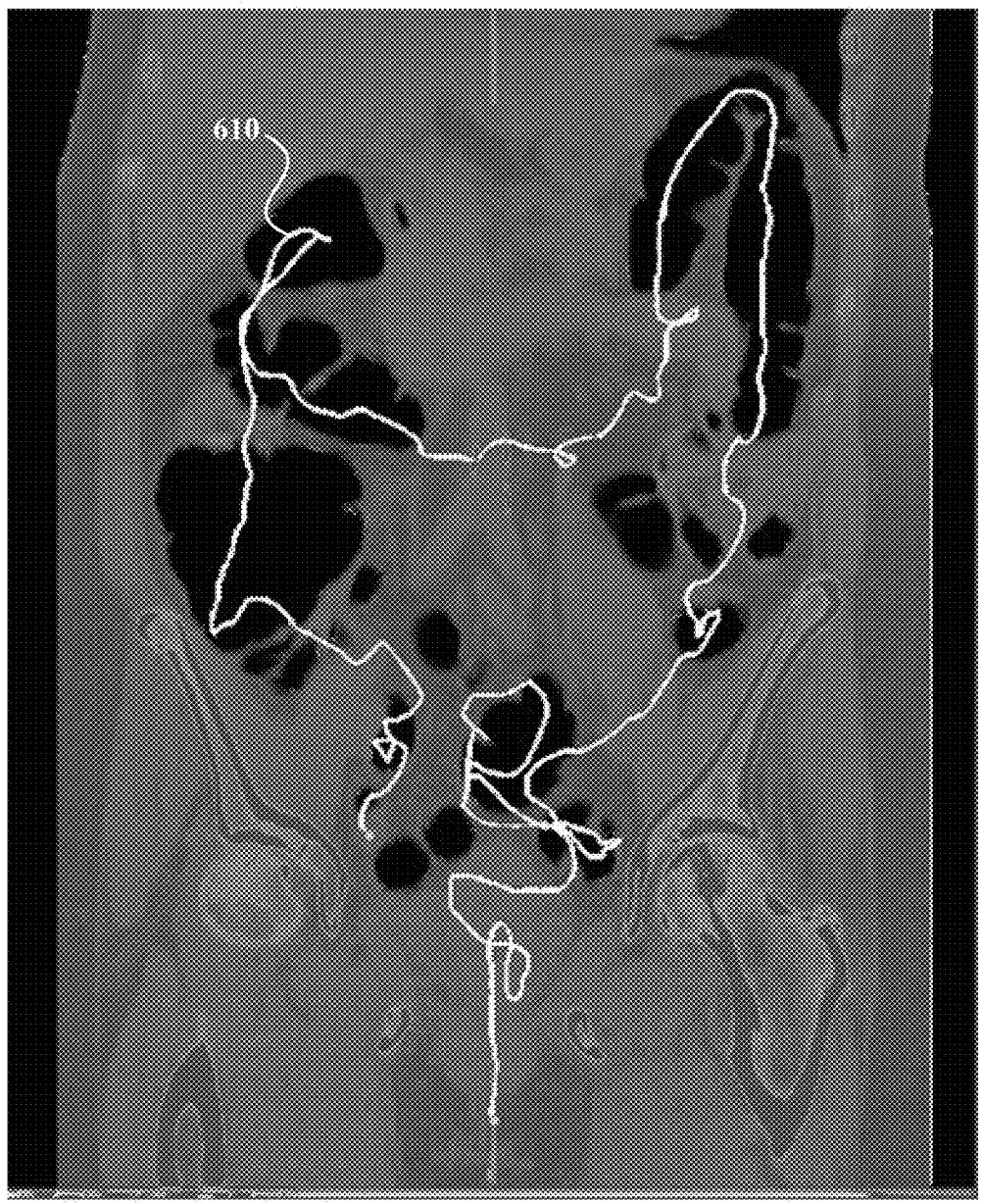
FIG. 6 is an illustration of a path along a centerline through the virtual colon of FIG. 5.

Because of the weight used, the optimal path will travel along the center-line of the virtual model. FIG. 6 illustrates the center line or identified end-to-end path, identified using the described process. The path 610 is illustrated in white in FIG. 6, as overlayed on an abdominal image of a human. The path 610 may represent the centerline or view point path through the virtual model and may be used to enable a virtual fly-through of the center of the colon.

Figure 7A:
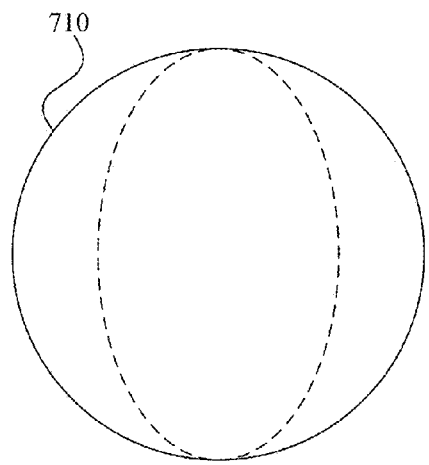
FIGS. 7a-7c illustrate the use of spherical shells in imaging a virtual colon in accordance with an example of the present technology.

Once a virtual model has been identified, as well as a centerline through the virtual model, images may be captured or rendered from a virtual observer or view point on the centerline within the virtual model. For example, image points may be rendered in a spherical coordinate system. In other words, image points may be generated using concentric spherical shells around the virtual observer or view point that flies through the colon. FIG. 7a illustrates a single example spherical shell 710.

A spherical coordinate system may be a coordinate system for three-dimensional space where the position of a point is specified by three numbers: the radial distance of that point from a fixed origin (i.e., the centerline), a polar angle of the point measured from a fixed zenith direction, and the azimuth angle of an orthogonal projection of the point on a reference plane that passes through the origin and is orthogonal to the zenith, measured from a fixed reference direction on that plane. To define a spherical coordinate system, two orthogonal directions, the zenith and the azimuth reference may be selected, as well as the origin point. This selection may determine a reference plane that contains the origin and is perpendicular to the zenith. The spherical coordinates of a point P may then be defined as follows:

a radius or radial distance may be a Euclidean distance from the origin O to P.

an inclination (or polar angle) may be an angle between the zenith direction and the line segment OP.

an azimuth (or azimuthal angle) may be a signed angle measured from the azimuth reference direction to the orthogonal projection of the line segment OP on the reference plane.

In one example, the spherical coordinates of the spherical shells may be mapped to a rectangular window or two-dimensional (2D) window such that the azimuth angle is mapped to the x-axis of the 2D window, the inclination angle is mapped to the y-axis of the 2D window, and the radius provides "depth" in 3D rendering. For example, spherical shells may be mapped to a cylindrical projection "wrapped" around the spherical shells and then "unrolled". For example, a Mercator cylindrical projection may be used where meridians of the spherical shells are mapped to equally spaced vertical lines, and circles of latitude or parallels are mapped to horizontal lines. The Mercator projection shows courses of constant bearing as straight lines when mapped to the rectangular two-dimensional view. Other cylindrical, pseudo-cylindrical, or other projections may also be used to map a three dimensional spherical image to a two-dimensional image.

The spherical coordinates may be selected to enable rendering of greater than 360° for the azimuth angle in order to show "overlap" on the side edges of the panoramic peripheral image. In other words, while a conventional sphere may include 360°, virtual spherical shells may be configured to display greater than 360°. For example, considering mapping to a cylinder that is then unwrapped at a "seam" defining edges of what will be sides of a 2D view, the edges may overlap at the seam, and the portion of the overlap may include the same image data.

Figure 7B:
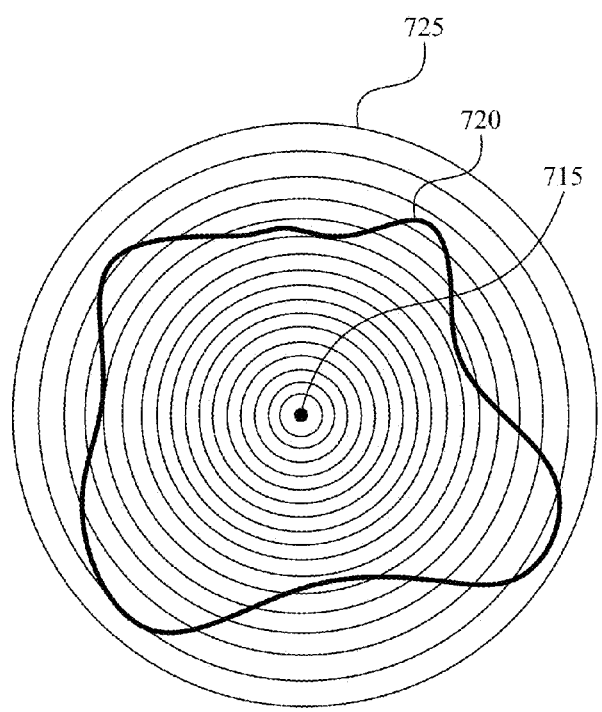

Referring to FIG. 7b, a plurality of concentric spherical shells 725 are shown in a cross-sectional view relative to a colon model 720. The concentric spherical shells may be nested shells and may be centered around a centerline 715 of the colon model 720. Any number of spherical shells 725 may be implemented. The number and spacing of the spherical shells 725 in FIG. 7b is intended for illustration purposes and is not intended to be limiting.

Each spherical shell may represent a slice or layer of what might be a spherical view from the virtual observer at the centerline. The spherical shells may be generated outwardly from the virtual observer until each portion of the virtual model is included in at least one spherical shell. The spherical shells, when stacked together, may represent a 3D geometry of the colon model as viewed from the virtual observer, and individual spherical shells may include a slice of the geometry or a portion of the stack forming the geometry. Portions of the spherical shell images may be transparent or devoid of color or other image data where portions of the colon model are not present. Portions of the spherical shell images where a portion of the colon model is present may be colorized, solid or non-transparent.

The 3D spherical view from the point of view of the virtual observer may be constructed in reverse order from an outermost spherical shell toward the virtual observer. Some image data on inner shells may occlude image data on outer shells as the spherical shells are stacked inwardly, and the inner layers may occlude viewing of image data covered over from the outer layers.

A 3D spherical image may be generated based on the 3D spherical view from the point of view of the virtual observer and may be mapped to the two dimensional panoramic view. The anterior and posterior views from the virtual observer may be included in the 2D view as a result of being located at polar ends or coordinates of the spherical shells along the longitudinal axis or centerline. In one aspect, rather than creating a 3D spherical image based on the 3D spherical view from the point of view of the virtual observer, each of the shells may be laid out in the 2D window using cylindrical projection and stacked from the outside toward the virtual observer.

The mapping of the spherical shells to the 2D image may result in some distortion of the image, such as at the top and/or bottom edges of the image for example, but distortion may be minimal because the imaged lumen or colon is cylindrical and the spherical shells are mapped using cylindrical projection.

Figure 7C:
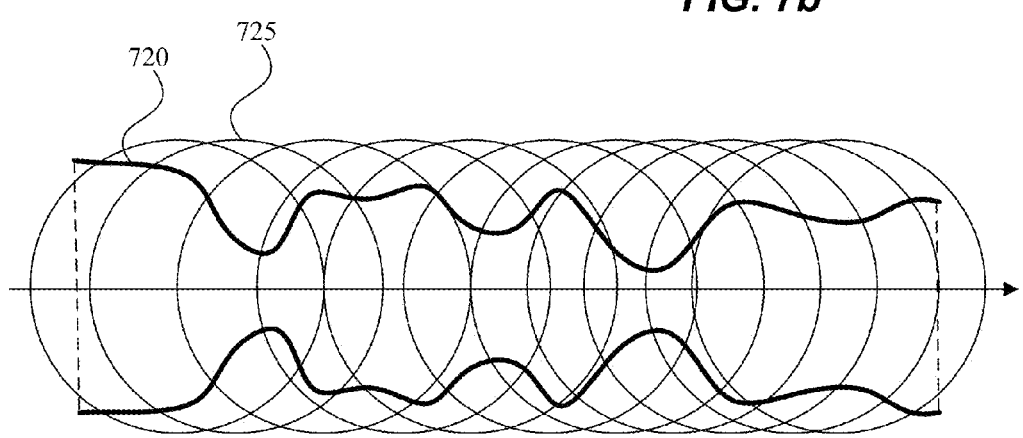

FIG. 7c illustrates a cross-sectional side view of a colon 720 where the process of creating cylindrical shells 725 to generate panoramic peripheral views of the colon is repeated at intervals along the colon 720. FIG. 7c illustrates the outer shell of the shell set for multiple positions of the view point. The smaller the intervals between the spherical shells 725, the more completely the areas of the colon may be viewed by a medical professional navigating the colon 720 in a virtual colonoscopy in terms of being able to stop at and/or view any desired location along the virtual colon 720. The creation of spherical shell images and rendering of the 2D images based on the spherical shell images may be performed in advance of a virtual colonoscopy examination or may be performed on demand according to navigation instructions received during the virtual colonoscopy examination.

Other example methods of generating linear panoramic peripheral images are also contemplated. Some examples of seamed and seamless arrangement of captured images have been described previously. Some additional examples may include raycasting, volumetric rendering and so forth. In one example, two dimensional peripheral images of a virtual model may be mapped to 3D spherical coordinates with regions of overlap to minimize distortions and then the peripheral images may be mapped back to a 2D view using cylindrical projection. Any number of other variations of generating linear panoramic peripheral images may also be performed and are considered to be within the scope of this disclosure.

Lighting, reflections, shadows and the like may be added to a virtual scene to improve visibility of features and enhance the effect of navigating along a three dimensional model. When a patient undergoes scanning to obtain images for use in a virtual colonoscopy, pools of liquid may be present in the colon. Such pools of liquid may appear as a bulge or area of higher reflectivity of light. Pools of liquid may obscure or hinder a clear view of features underneath the liquid. In some examples, light filters may be applied to the panoramic image to enable at least partial viewing of features potentially hidden behind the liquid.

Figure 8A:
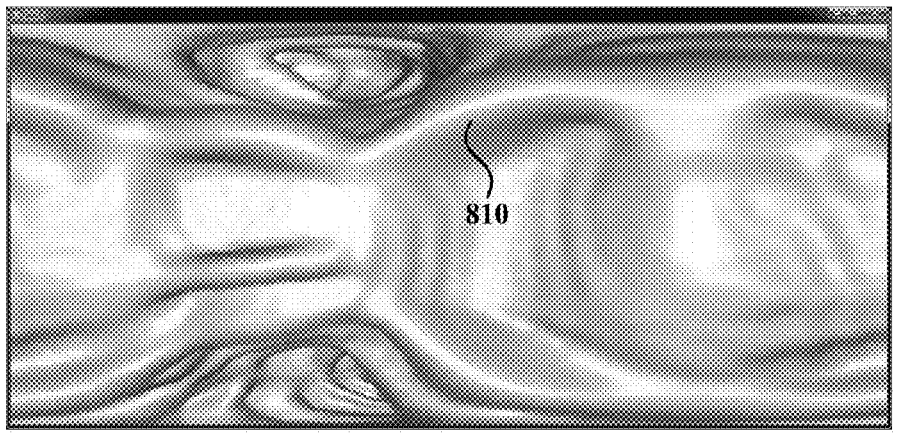
FIGS. 8a-8c depict a rolling effect of a panoramic peripheral image as a virtual observer is moved along a path in a virtual model in accordance with an example of the present technology.
Figure 8B:
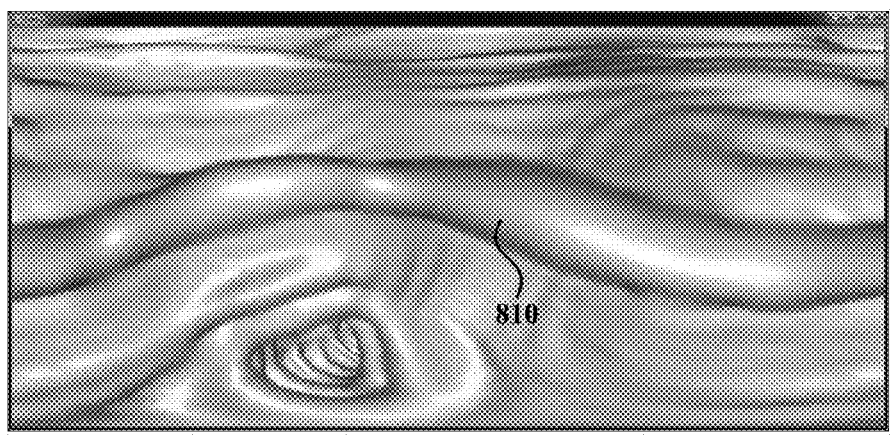
Figure 8C:
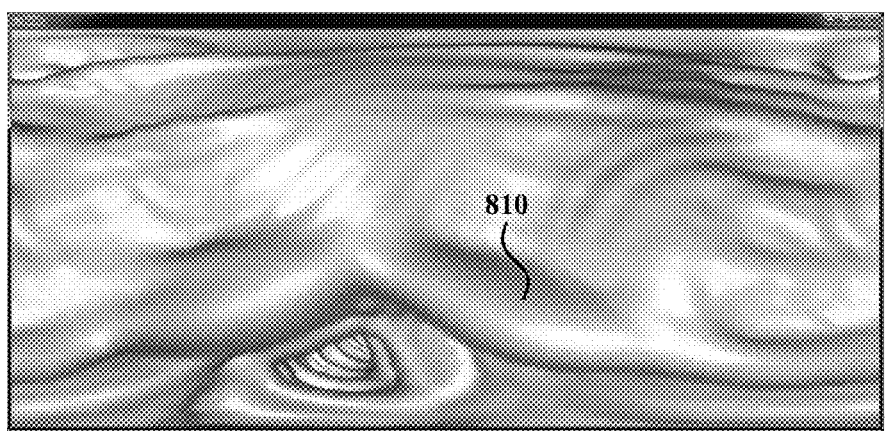

Referring to FIGS. 8a-8c, sequential panoramic peripheral views of a virtual colon are shown. A result of the use of spherical shells mapped to the 2D view is that progression along the path within the virtual colon causes the colon to appear to roll past a view. For example, in FIG. 8a an anterior view is shown near the top of the image and a posterior view is shown near a bottom of the image. A peripheral side view is shown along a center of the image, being centered between the top and bottom of the image. As the virtual observer or point of view is shifted toward the anterior direction, features of the virtual model shown near a top of the image will progress toward the center of the image and then proceed toward the bottom of the image and eventually out of view in the posterior direction.

The rolling effect may enhance an ability of a medical professional to analyze the virtual model from virtually every angle. For example, as the virtual observer is moved along the defined centerline path, a ridge 810 or other structure within the colon may appear at a side of the image with a first side of the ridge 810 fully visible, as in FIG. 8a. As the virtual observer is moved further along the path, the ridge 810 may move toward the center of the image, such that a top of the ridge 810, and potentially both sides of the ridge 810 may be simultaneously visible, including the first side and an opposite second side. As the virtual observer is moved even further along the path, the ridge 810 may move toward the bottom of the image and the second side may remain visible while the first side becomes hidden from view as the ridge 810 rolls past. The rolling effect further enables full view of "valleys" between ridges for convenience in examination.

The present technology has been described primarily in terms of examination of human or animal organs, and specifically in terms of a colon for purposes of a virtual colonoscopy. However, the technology may be applied in any of a number of other fields as well, including but not limited to imaging of lumens, respiratory tracts, and other cylindrical type structures. Furthermore, the technology may be applied for imaging of non-cylindrical structures or scenes, including scenes without specific definition of bounds, but may preferably be used where a path is defined as well as an extent outwardly from a virtual observer to which shells or other imaging processes are to be applied.

Figure 9:
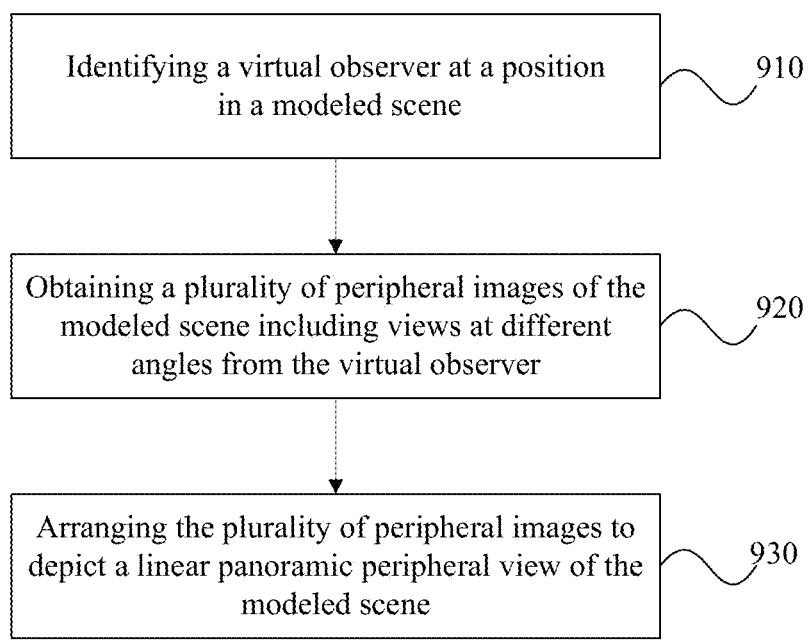
FIG. 9 is a flow diagram of a method for creating a panoramic peripheral image in accordance with an example of the present technology.

Referring now to FIG. 9, a flow diagram for creating a panoramic peripheral image is illustrated in accordance with an example of the present technology. The method may include identifying 910 a virtual observer or view point at a position in a modeled scene. Peripheral images of the modeled scene may be obtained 920, including views at different or multiple angles from the virtual observer. It is noted that, as one example, a spherical image includes views at different angles from the virtual observer and the nested or concentric spherical shell images may represent the plurality of peripheral images including the views at the different angles. The peripheral images may be arranged 930 to depict a linear or strip panoramic peripheral view of the modeled scene. This arrangement may be, for example, a matter of arranging a plurality of 2D peripheral images linearly to collectively form a panorama or may include mapping of stacked spherical images to a 2D view. The method may include other example implementations, as have been described.

The method may include generating coordinates or image points for the modeled scene in a spherical coordinate system around the virtual observer. The coordinates or image points may be mapped to a two-dimensional view and the panoramic peripheral image may be created as a seamless panoramic peripheral image from the spherical coordinate system based on the mapping of the coordinates to the two-dimensional view. In a specific implementation, mapping of the coordinates to the two-dimensional view may include mapping an azimuth angle to an x-axis, an inclination angle to a y-axis and using a radius of the spherical coordinate system for depth in rendering the panoramic peripheral image.

In one example, obtaining the peripheral images of the scene may include obtaining peripheral images substantially perpendicular to an axis in an axial direction in the scene. The axis may be the centerline and the axial direction may be the path followed by the centerline or predefined path through the colon. The method may include obtaining axial images of the scene in opposing axial directions along the axis, such as in the anterior and posterior directions. These axial images may be provided for display in a display window together with the panoramic peripheral image. Sizes of the axial images relative to the panoramic peripheral image may vary depending on a specific application or upon individual preferences. In one aspect, the inclusion of the axial images with the panoramic peripheral image as well as configuration of the relative sizes of the axial images to the panoramic peripheral image may be user-definable. For example, the axial images may, combined, occupy a smaller portion of the display window than the panoramic peripheral image, or may occupy a same size portion of the display window as the panoramic peripheral image, or may occupy a larger portion of the display window than the panoramic peripheral image.

Figure 10:
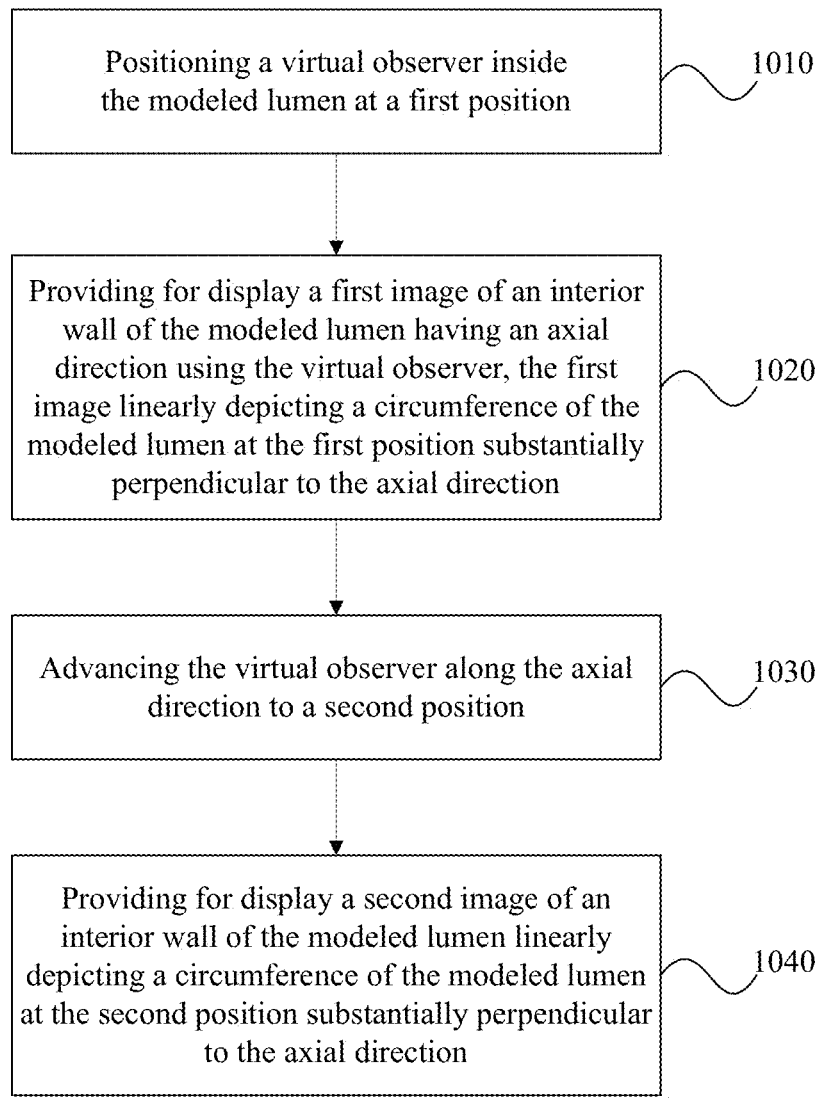
FIG. 10 is a flow diagram of a method for viewing a modeled lumen in accordance with an example of the present technology.

Referring to FIG. 10, a flow diagram of a method of viewing a modeled lumen is illustrated in accordance with an example of the present technology. An example of a lumen may be a central cavity of a tubular or other hollow structure, such as in an organism or cell. Some more specific examples of lumina include arteries, veins, intestines or other gastrointestinal tracts, endoplasmic reticulum, the pathways of the bronchi in the lungs, the interior of renal tubules and urinary collecting ducts, pathways of genital or reproductive tracts and so forth.

The method may include positioning 1010 a virtual observer or view point inside the modeled lumen at a first position. A first image of an interior wall of the modeled lumen may be provided for display 1020, the first image having an axial direction as determined according to a path of a centerline or travel path through the modeled lumen. The first image may linearly depict a circumference of the modeled lumen at the first position with a viewpoint substantially perpendicular to the axial direction. The first image may further optionally include one or more viewpoints substantially parallel with the axial direction (see, for example, FIG. 8a where the viewpoint substantially perpendicular to the axial direction is shown at a center of the image and opposing viewpoints substantially parallel with the axial direction are shown near the edges of the image (i.e., the top and bottom sides of the image)).

The method may include advancing 1030 the virtual observer along the axial direction to a second position and providing for display 1040 a second image of an interior wall of the modeled lumen linearly depicting a circumference of the modeled lumen at the second position substantially perpendicular to the axial direction.

In one example, providing the image of the interior wall of the modeled lumen depicting the circumference of the modeled lumen at the first position comprises providing, for display, a single image depicting at least a 360° seamless view of the interior wall of the modeled lumen. The single image may optionally include a greater than 360° view of the interior wall of the modeled lumen. In another example, the image of the interior wall may comprise a plurality of images arranged linearly or in a strip to depict a circumference or peripheral view of the lumen.

The first and second images of the method may be images in a sequence of images depicting features on the interior wall of the modeled lumen. The method may include advancing the observer along the axial direction and providing the sequence of images for display in sequence such that a feature in a current image of the sequence of images rolls past a center of the sequence of images as the observer is advanced, the center of the images being a center between two opposing sides of the images. In a specific implementation, the feature (such as a ridge, for example) may be depicted on a first edge of the sequence of images (such as the top, for example) with a first side of the feature visible and a second side of the feature hidden from view. The feature may be subsequently depicted near the center of the sequence of images after depicting the feature near the first edge, such that the first side and the second side of the feature are visible. Subsequently, the feature may be depicted near a second edge of the sequence of images (such as the bottom side, for example) with the second side of the feature visible and the first side of the feature hidden from view.

Figure 11:
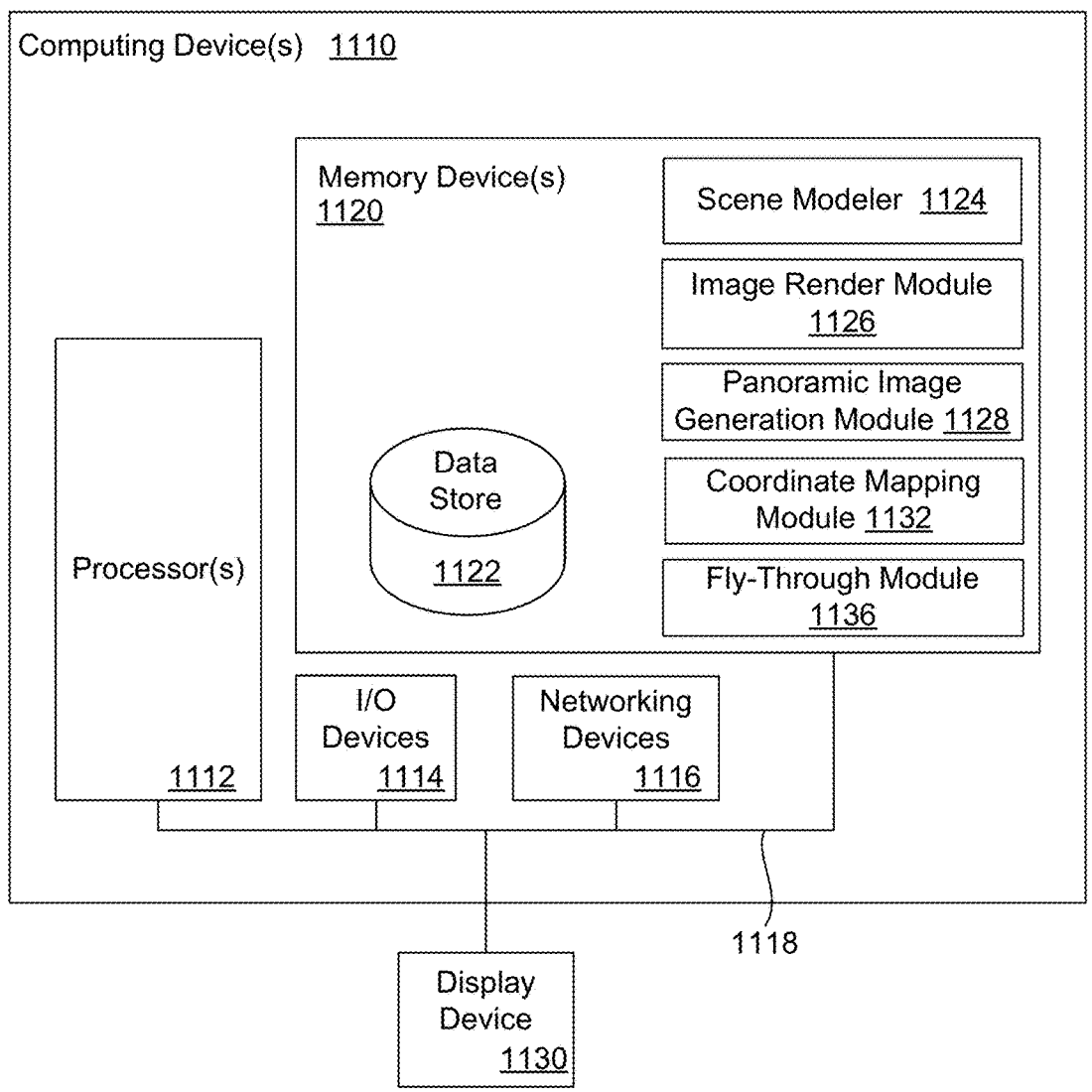
FIG. 11 is a block diagram of a productivity monitoring system in accordance with an example of the present technology.

Referring to FIG. 11, a block diagram of a panoramic image generation system system is illustrated in accordance with an example. The system may include a scene modeler 1124 for modeling a scene based on a series of two-dimensional image slices of the scene, such as images slices obtained from a CT scan for example. In another example, the scene modeler 1124 may be configured to model a scene based on three-dimensional image data or other image data. The system may include an image render module 1126 for rendering a plurality of peripheral images of the scene including views at different angles from a virtual observer within the scene. In one aspect, peripheral images may be off-axis to an axis in an axial direction extending between anterior and posterior portions of the scene. The peripheral images may collectively include at least a 360° peripheral view of the scene. A panoramic image generation module 1128 may be used for generating a linear or strip panoramic peripheral image of the scene based on an output from the image render module.

The system may include a coordinate mapping module 1132 for generating coordinates for a spherical shell images in a spherical coordinate system and for mapping the coordinates of the spherical shells to a two-dimensional view.

The system may include a fly-through module 1136 to enable a user to virtually move through the scene along the axial direction. The configuration of the images and the fly-through module may result in features of the scene appearing to roll past the user as the user virtually moves through the scene.

The system may include a display device 1130 configured to display the rendered panoramic images for viewing by a medical professional. The display device may also be configured to display a graphical user interface by which the medical professional may interact with the model of the scene, such as for purposes of examining the model.

The panoramic image generation module 1128 may be configured for rendering the 2D panoramic peripheral image with a 3D effect. For example, lighting effects may be applied to the image, creating shadows, reflections and so forth. As another example, the linear panoramic peripheral image may be created as a stereo image or other 3D image, which may optionally be best viewed with 3D glasses or the like to view the 3D effect of the image.

The modules that have been described may be stored on, accessed by, accessed through, or executed by a computing device 1110. The computing device 1110 may comprise any system providing computing capability. The computing device 1110 may be embodied, for example in the form of a client computer, a desktop computer, a laptop computer, a mobile device, a hand held messaging device, a set-top box, heads up display (HUD) glasses, a car navigation system, personal digital assistants, cellular telephones, smart phones, set-top boxes, network-enabled televisions, music players, web pads, tablet computer systems, game consoles, electronic book readers or other devices with like capability, including capabilities of receiving and presenting content from a server. The computing device 1110 may include a display 1130. The display 1130 may comprise, for example, one or more devices such as cathode ray tubes (CRTs), liquid crystal display (LCD) screens, gas plasma based flat panel displays, LCD projectors, or other types of display devices, etc.

In one aspect, a plurality of computing devices may be employed that are arranged, for example, in one or more server banks, blade servers or other arrangements. For example, a plurality of computing devices together may comprise a cloud computing resource, a grid computing resource, and/or any other distributed computing arrangement. Such computing devices may be located in a single installation or may be distributed among many different geographical locations. For purposes of convenience, the computing device 1110 is referred to herein in the singular form. Even though the computing device 1110 is referred to in the singular form, however, it is understood that a plurality of computing devices may be employed in the various arrangements described above.

Various applications and/or other functionality may be executed in the computing device 1110 according to various embodiments, which applications and/or functionality may be represented at least in part by the modules that have been described. Also, various data may be stored in a data store 1122 that is accessible to the computing device. The data store 1122 may be representative of a plurality of data stores as may be appreciated. The data stored in the data store 1122, for example, is associated with the operation of the various applications and/or functional entities described. The components executed on the computing device 1110 may include the modules described, as well as various other applications, services, processes, systems, engines or functionality not discussed in detail herein.

The term "data store" may refer to any device or combination of devices capable of storing, accessing, organizing and/or retrieving data, which may include any combination and number of data servers, relational databases, object oriented databases, simple web storage systems, cloud storage systems, data storage devices, data warehouses, flat files and data storage configuration in any centralized, distributed or clustered environment. The storage system components of the data store may include storage systems such as a SAN (Storage Area Network), cloud storage network, volatile or non-volatile RAM, optical media or hard-drive type media.

The computing device 1110 may be representative of a plurality of local client devices that may be coupled to a network. The client devices may communicate over any appropriate network, including an intranet, the Internet, a cellular network, a local area network (LAN), a wide area network (WAN), a wireless data network or a similar network or combination of networks.

Although a specific structure may be described herein that defines server-side roles (e.g., roles of the management device) and client-side roles (e.g., roles of the local computing device), it is understood that various functions may be performed at the server side or the client side.

Certain processing modules may be discussed in connection with this technology. In one example configuration, a module may be considered a service with one or more processes executing on a server or other computer hardware. Such services may be centrally hosted functionality or a service application that may receive requests and provide output to other services or customer devices. For example, modules providing services may be considered on-demand computing that is hosted in a server, cloud, grid or cluster computing system. An application program interface (API) may be provided for each module to enable a second module to send requests to and receive output from the first module. Such APIs may also allow third parties to interface with the module and make requests and receive output from the modules. Third parties may either access the modules using authentication credentials that provide on-going access to the module or the third party access may be based on a per transaction access where the third party pays for specific transactions that are provided and consumed.

The computing device 1110 may include one or more processors 1112 that are in communication with memory devices 1120. The computing device 1110 may include a local communication interface for the components in the computing device 1110. For example, the local communication interface may be a local data bus 1118 and/or any related address or control busses as may be desired.

The memory device 1120 may contain modules that are executable by the processor(s) and data for the modules. Located in the memory device 1120 are modules executable by the processor 1112. The data store 1122 may also be located in the memory device 1120 for storing data related to the modules and other applications along with an operating system that is executable by the processor(s) 1112.

Various applications may be stored in the memory device and may be executable by the processor(s) 1112. Components or modules discussed in this description that may be implemented in the form of software using high programming level languages that are compiled, interpreted or executed using a hybrid of the methods.

The computing device 1110 may also have access to I/O (input/output) devices 1114 that are usable by the computing devices 1110. An example of an I/O device 1114 is a display screen that is available to display output from the computing devices. Other known I/O devices 1114 may be used with the computing device 1110 as desired. Networking devices 1116 and similar communication devices may be included in the computing device 1110. The networking devices 1116 may be wired or wireless networking devices that connect to the internet, a LAN, WAN, or other computing network.

The components or modules that are shown as being stored in the memory device 1120 may be executed by the processor 1112. The term "executable" may mean a program file that is in a form that may be executed by a processor. For example, a program in a higher level language may be compiled into machine code in a format that may be loaded into a random access portion of the memory device and executed by the processor, or source code may be loaded by another executable program and interpreted to generate instructions in a random access portion of the memory to be executed by a processor. The executable program may be stored in any portion or component of the memory device. For example, the memory device may be random access memory (RAM), read only memory (ROM), flash memory, a solid state drive, memory card, a hard drive, optical disk, floppy disk, magnetic tape, or any other memory components.

The processor 1112 may represent multiple processors and the memory may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology. As used herein, the terms "medium" and "media" may be interchangeable with no intended distinction of singular or plural application unless otherwise explicitly stated. Thus, the terms "medium" and "media" may each connote singular and plural application.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The invention claimed is:

1. A method of creating a panoramic peripheral image, comprising:
identifying a virtual observer at a position in a modeled scene;
rendering a three-dimensional spherical view from a viewpoint of the virtual observer using rendered concentric, nested spherical shells each representing a slice of the spherical view, wherein the spherical shells are assembled in a reverse order from an outermost shell toward the virtual observer, wherein portions of one or more of the spherical shells occlude portions of one or more larger, outward spherical shells;
generating coordinates for the modeled scene in a spherical coordinate system around the virtual observer;
mapping the coordinates to a two-dimensional view;

obtaining a plurality of peripheral images of the modeled scene from the two-dimensional view, including views at multiple angles from the virtual observer;

arranging the plurality of peripheral images to depict a linear strip panoramic peripheral view of the modeled scene; and creating the linear strip panoramic peripheral view as a seamless panoramic peripheral image from the spherical coordinate system based on the mapping of the coordinates to the two-dimensional view by stitching the images together using image processing to smooth edges and match coloration of adjacent of the plurality of peripheral images;

wherein the linear strip panoramic peripheral view includes greater than a 360° view of the scene with overlap portions at side edges of the seamless panoramic peripheral image, and wherein top, bottom, left and right views are included in the panoramic peripheral image.

2. The method of claim 1, wherein mapping the coordinates to the two-dimensional view comprises mapping the spherical shells to a Mercator cylindrical projection wrapped around the spherical shells.

3. The method of claim 1, wherein the plurality of peripheral images comprise two-dimensional images of the modeled scene, the modeled scene being three-dimensional, the method further comprising mapping the two-dimensional images to three-dimensional coordinates with regions of overlap to minimize distortion, and mapping the two-dimensional images having the three-dimensional coordinates to a two-dimensional view using a cylindrical projection.

4. The method of claim 1, wherein the plurality of peripheral images comprises three-dimensional concentric shells centered around the virtual observer.

5. The method of claim 1, wherein obtaining the plurality of peripheral images of the scene comprises obtaining the plurality of peripheral images substantially perpendicular to an axis in an axial direction in the scene.

6. The method of claim 1, wherein the seamless panoramic peripheral image seamlessly includes anterior and posterior axial views respectively arranged proximal to opposing edges of the panoramic peripheral image.

7. The method of claim 1, further comprising applying a light filter to the seamless panoramic peripheral image to enable at least partial visibility of features behind liquid in a colon represented by the seamless panoramic peripheral image.

8. A panoramic image generation system, comprising:

a scene modeler to model a scene based on a series of two-dimensional image slices of the scene;

an image render module to:

render a three-dimensional spherical view from a viewpoint of the virtual observer using rendered concentric, nested spherical shells each representing a spherical slice of the spherical view, wherein the spherical shells are assembled in a reverse order from an outermost shell toward the virtual observer, wherein portions of one or more of the spherical shells occlude portions of one or more larger, outward spherical shells;

generate coordinates for the modeled scene in a spherical coordinate system around the virtual observer;

map the coordinates to a two-dimensional view; and render a plurality of peripheral images of the scene including views at different angles from the virtual observer within the scene based on the mapping of the coordinates to the two-dimensional view; and a panoramic image generation module to generate a linear panoramic peripheral image strip of the scene based on an output from the image render module, wherein the panoramic peripheral image strip includes greater than a 360° view of the scene with overlap portions at side edges of the panoramic peripheral image and wherein top, bottom, left and right views are included in the linear strip panoramic peripheral view, the panoramic image generation module further configured to generate the linear strip panoramic peripheral view as a seamless panoramic peripheral image by stitching the plurality of peripheral images together using image processing to smooth edges and match coloration of adjacent of the plurality of peripheral images.

9. The system of claim 8, wherein the plurality of peripheral images are off-axis to an axis in an axial direction extending between anterior and posterior portions of the scene, the plurality of peripheral images collectively including at least a 360° peripheral view of the scene.

10. The system of claim 9, further comprising a fly-through module for enabling a user to virtually move through the scene along the axial direction, wherein features of the scene appear to roll past the user as the user virtually moves through the scene.

* * * * *